US009949609B2

(12) United States Patent
Baer et al.

(10) Patent No.: US 9,949,609 B2
(45) Date of Patent: *Apr. 24, 2018

(54) WATER DISPERSIBLE WIPE SUBSTRATE

(71) Applicant: Georgia-Pacific Consumer Products LP, Atlanta, GA (US)

(72) Inventors: Samuel Charles Baer, Atlanta, GA (US); Joseph H. Miller, Neenah, WI (US)

(73) Assignee: GPCP IP Holdings LLC, Atlanta, GA (US)

( * ) Notice: Subject to any disclaimer, the term of this patent is extended or adjusted under 35 U.S.C. 154(b) by 821 days.

This patent is subject to a terminal disclaimer.

(21) Appl. No.: 14/200,320

(22) Filed: Mar. 7, 2014

(65) Prior Publication Data
US 2014/0259484 A1 Sep. 18, 2014

Related U.S. Application Data

(60) Provisional application No. 61/792,801, filed on Mar. 15, 2013.

(51) Int. Cl.
| A47L 13/16 | (2006.01) |
|---|---|
| A47L 13/17 | (2006.01) |
| D04H 3/015 | (2012.01) |
| D04H 3/11 | (2012.01) |
| D04H 3/12 | (2006.01) |
| D21H 27/00 | (2006.01) |
| A61Q 19/00 | (2006.01) |
| A61Q 19/10 | (2006.01) |
| A61K 8/02 | (2006.01) |

(52) U.S. Cl.
CPC .............. *A47L 13/16* (2013.01); *A47L 13/17* (2013.01); *A61K 8/0208* (2013.01); *A61Q 19/00* (2013.01); *A61Q 19/005* (2013.01); *A61Q 19/10* (2013.01); *D04H 3/015* (2013.01); *D04H 3/11* (2013.01); *D04H 3/12* (2013.01); *D21H 27/002* (2013.01)

(58) Field of Classification Search
CPC ......... A47L 13/16; A47L 16/17; A61Q 19/00; A61Q 19/005; A61Q 19/10; D04H 3/015; D04H 3/11; D04H 3/12
See application file for complete search history.

(56) References Cited

U.S. PATENT DOCUMENTS

| 797,749 A | 8/1905 | Robinson et al. |
|---|---|---|
| 2,045,095 A | 7/1934 | Osborne |
| 2,407,227 A | 11/1943 | Earle |
| 2,689,199 A | 9/1954 | Pesce |
| 3,301,746 A | 1/1967 | Sanford et al. |
| 3,485,706 A | 12/1969 | Evans |
| 3,785,922 A | 5/1970 | Keller |
| 3,554,862 A | 1/1971 | Hervey et al. |
| 3,563,241 A | 2/1971 | Evans |
| 3,849,241 A | 11/1974 | Butin et al. |
| 3,917,785 A | 11/1975 | Kalwaites |
| 4,014,635 A | 3/1977 | Kroyer |
| 4,081,319 A | 3/1978 | Conway |
| 4,100,324 A | 7/1978 | Anderson et al. |
| 4,144,122 A | 3/1979 | Emanuelsson et al. |
| 4,200,488 A | 4/1980 | Brandon et al. |
| 4,442,161 A | 4/1984 | Kirayoglu et al. |
| 4,469,734 A | 9/1984 | Minto et al. |
| 4,476,323 A | 10/1984 | Hellsten et al. |
| 4,559,157 A | 12/1985 | Smith et al. |
| 4,617,383 A | 10/1986 | Jaskowski |
| 4,640,810 A | 2/1987 | Laursen et al. |
| 4,667,890 A | 5/1987 | Gietman, Jr. |
| 4,690,821 A | 9/1987 | Smith et al. |
| 4,755,421 A | 7/1988 | Manning et al. |
| 4,787,699 A | 11/1988 | Moulin |
| 4,795,476 A | 1/1989 | Bean et al. |
| 4,808,467 A | 2/1989 | Suskind et al. |
| 4,818,464 A | 4/1989 | Lau |
| 5,205,835 A | 4/1993 | Tieckelmann et al. |
| 5,284,703 A | 2/1994 | Everhart et al. |
| 5,292,581 A | 3/1994 | Viazmensky et al. |
| 5,350,624 A | 9/1994 | Georger et al. |
| 5,389,202 A | 2/1995 | Everhart et al. |
| 5,573,637 A | 11/1996 | Ampulski et al. |
| 5,674,591 A | 10/1997 | James et al. |

(Continued)

FOREIGN PATENT DOCUMENTS

| CA | 841938 A | 5/1970 |
|---|---|---|
| CN | 1299422 A | 6/2001 |

(Continued)

OTHER PUBLICATIONS

Chinese Search Report dated Mar. 3, 2016 for Application No. 201380046325.7.
European Search Report dated Mar. 22, 2016 for Application No. 13835305.7-1308 / 2893068.
Batra, Subhash Kumar, et al.; "Introduction to Nonwovens Technology"; DEStech Publications, Inc.; p. 131-160; 2012.
Chemical Week Publication; "New Chemical Perspectives"; Soap and Cosmetics; p. 4, p. 12-13; Mar. 2000.
Floyd, Don E.; "Polyamide Resins"; Reinhold Publishing Corporation; p. 1-227; 1996.
International Search Report and Written Opinion dated Dec. 3, 2013 for Application No. PCT/US2013/057228.
Lee et al., "Antimicrobial and Blood Repellent Finishes for Cotton and Nonwoven Fabrics Based on Chitosan and Fluropolymers", Textile Research Journal, 69 (2), Feb. 1999; pp. 104-112.

(Continued)

*Primary Examiner* — Jeremy R Pierce
(74) *Attorney, Agent, or Firm* — Ram W. Sabnis

(57) ABSTRACT

Water dispersible nonwoven substrates in accordance with the present invention are formed primarily of individualized bast fibers substantially free of pectin. The nonwoven substrate can include staple fibers to a lesser extent than the individualized bast fibers. Individualized bast fibers include fibers derived from the flax and hemp plants. The nonwoven substrate is formed into a web in a wet or a dry state and subsequently bonded to produce a water dispersible nonwoven substrate. The nonwoven substrate can be a tissue or a wet wipe.

80 Claims, No Drawings

(56) References Cited

U.S. PATENT DOCUMENTS

| | | |
|---|---|---|
| 5,683,794 A | 11/1997 | Wadsworth et al. |
| 5,695,868 A | 12/1997 | McCormack |
| 5,853,538 A | 12/1998 | Reiner |
| 5,891,126 A | 4/1999 | Osborn, III et al. |
| 5,948,710 A | 9/1999 | Pomplun et al. |
| 5,958,186 A | 9/1999 | Holm et al. |
| 5,985,186 A | 11/1999 | Kasprzyk et al. |
| 6,037,407 A | 3/2000 | Derian et al. |
| 6,051,749 A | 4/2000 | Schulz |
| 6,163,943 A | 12/2000 | Johansson et al. |
| 6,423,397 B1 | 11/2002 | Roussel |
| 6,713,413 B2 | 3/2004 | Kruegler |
| 6,762,138 B2 | 7/2004 | Ferreira et al. |
| 6,884,837 B2 | 4/2005 | Kohlhammer et al. |
| 6,994,865 B2 | 2/2006 | Branham et al. |
| 7,432,219 B2 | 10/2008 | Strandqvist et al. |
| 7,481,843 B2 | 1/2009 | Xu |
| 7,546,698 B2 | 6/2009 | Meschter |
| 7,732,357 B2 | 6/2010 | Annis et al. |
| 7,772,138 B2 | 8/2010 | Lostocco et al. |
| 7,892,397 B2 | 2/2011 | Luo et al. |
| 7,932,196 B2 | 4/2011 | McCormack et al. |
| 8,133,825 B2 | 3/2012 | Bunyard et al. |
| 8,287,986 B2 | 10/2012 | Huss et al. |
| 8,293,072 B2 | 10/2012 | Super et al. |
| 8,591,701 B2 | 11/2013 | Sung et al. |
| 8,603,802 B2 | 12/2013 | Sung et al. |
| 2001/0027545 A1 | 10/2001 | Fujiwara |
| 2003/0065059 A1 | 4/2003 | Krishnaswamy |
| 2003/0100240 A1* | 5/2003 | Takai ............ D21H 25/005 442/408 |
| 2003/0211802 A1 | 11/2003 | Keck et al. |
| 2003/0215602 A1 | 11/2003 | Andersson et al. |
| 2005/0092417 A1 | 5/2005 | Billgren et al. |
| 2005/0136773 A1 | 6/2005 | Yahiaoui et al. |
| 2005/0136779 A1 | 6/2005 | Stralin et al. |
| 2005/0245151 A1 | 11/2005 | Annis et al. |
| 2005/0245161 A1 | 11/2005 | Sain et al. |
| 2008/0153375 A1 | 6/2008 | Wilfong et al. |
| 2008/0261476 A1 | 10/2008 | Strandqvist et al. |
| 2009/0092835 A1* | 4/2009 | Xu ............ D01C 1/02 428/401 |
| 2009/0104430 A1 | 4/2009 | Cordial et al. |
| 2010/0093245 A1 | 4/2010 | Bradley et al. |
| 2010/0130086 A1 | 5/2010 | Dorsey et al. |
| 2010/0147472 A1 | 6/2010 | Sung et al. |
| 2010/0203291 A1 | 8/2010 | Dyer et al. |
| 2010/0203306 A1 | 8/2010 | Fingal et al. |
| 2010/0240113 A1* | 9/2010 | Liu ............ D01C 1/04 435/189 |
| 2011/0057346 A1* | 3/2011 | Nunn ............ D04H 1/4274 264/103 |
| 2011/0236665 A1 | 9/2011 | Roque et al. |
| 2011/0250813 A1 | 10/2011 | Bradley et al. |
| 2011/0312066 A1* | 12/2011 | Sung ............ D01C 1/02 435/277 |
| 2012/0021171 A1 | 1/2012 | Riviere et al. |
| 2012/0046394 A1* | 2/2012 | Lu ............ C08K 7/02 524/9 |
| 2012/0144611 A1 | 6/2012 | Baker et al. |
| 2012/0199301 A1 | 8/2012 | Strandqvist |
| 2013/0198984 A1 | 8/2013 | Strandqvist |
| 2013/0220151 A1 | 8/2013 | Sauter et al. |
| 2014/0066872 A1* | 3/2014 | Baer ............ D04H 1/46 604/367 |

FOREIGN PATENT DOCUMENTS

| | | |
|---|---|---|
| EP | 0408199 A1 | 1/1991 |
| EP | 1090176 A1 | 4/2001 |
| EP | 1350456 A1 | 10/2003 |
| WO | 9710100 A1 | 3/1997 |
| WO | 9826808 A2 | 6/1998 |
| WO | 9937834 A1 | 7/1999 |
| WO | 199337834 | 7/1999 |
| WO | 03099886 A1 | 12/2003 |
| WO | 2005025865 A1 | 3/2005 |
| WO | 2007140054 A1 | 12/2007 |
| WO | 2007140578 A1 | 12/2007 |
| WO | 2011046478 A1 | 4/2011 |
| WO | 2011151748 A2 | 12/2011 |
| WO | 2012050494 A1 | 4/2012 |
| WO | 2013015735 A1 | 1/2013 |
| WO | 2014039361 A1 | 3/2014 |
| WO | 2015023558 A1 | 2/2015 |

OTHER PUBLICATIONS

International Search Report and Written Opinion dated Jun. 30, 2014 for Application No. PCT/US2014/021760.
International Search Report and Written Opinion dated Oct. 23, 2015 for Application No. PCT/US2015/044138.
International Search Report and Written Opinion dated Nov. 27, 2014 for Application No. PCT/US2014/050478.
International Search Report and Written Opinion dated Jul. 28, 2014 for Application No. PCT/US2014/021771.
Chinese Search Report dated Mar. 14, 2017.
European Extended Search Report dated Aug. 10, 2016.
Taiwanese Office Action dated Aug. 4, 2017.

* cited by examiner

WATER DISPERSIBLE WIPE SUBSTRATE

CROSS-REFERENCE TO RELATED APPLICATIONS

This application claims benefit of U.S. Provisional Patent Application Ser. No. 61/792,801, filed Mar. 15, 2013, which is incorporated herein in its entirety by reference.

TECHNICAL FIELD OF THE INVENTION

The present invention relates generally to wipe substrates. More specifically, the present invention relates to a water dispersible nonwoven wipe substrates.

BACKGROUND OF THE INVENTION

Disposable wipe and tissue products are convenient, relatively inexpensive, sanitary, and easy to use. Personal care wipes are convenient because they are portable, suitable for travel, and versatile. Examples of disposable wipes include wet wipes (or wipers), e.g., baby wipes and cosmetic wipes. In addition to personal care wipes, disposable household wipes include kitchen cleaning wipes and dusting wipes.

Although convenient, discarding of disposable wipes can be problematic when the wipe substrates are not biodegradable or not "flushable." "Flushable" refers to an ability to evacuate a toilet. Wipe substrates that are not biodegradable or flushable can accumulate in landfills. However, even "flushable" wipe substrates may not be made of materials that are substantially water dispersible. In particular, a wipe substrate's ability to evacuate a toilet can be merely due to small size. Thus, wipes that do not disintegrate or substantially disperse in water have disadvantages because they can plug screens and jam pumps in sewage treatment plants.

Accordingly, there is a need for a biodegradable, water dispersible wipe that employs a nonwoven substrate made of individualized, natural fibers having a length as small as 4 millimeters. It is to solving this problem the present invention is directed.

SUMMARY OF THE INVENTION

The present invention is directed to water dispersible nonwoven substrates. In one aspect, a water dispersible nonwoven substrate includes a majority of individualized bast fibers that are substantially straight, substantially pectin-free, and have a mean length greater than 4 millimeters (mm).

In another aspect, a water dispersible nonwoven substrate includes a majority of bast fibers that are non-cotton, plant-based, and substantially pectin-free and have a mean length greater than 4 mm.

Yet, in another aspect, a water dispersible nonwoven substrate includes individualized bast fibers with less than 20% of the pectin content of the naturally occurring bundled bast fiber from which the individualized bast fibers are derived. The individualized bast fibers are formed into an unbounded web in the dry state, and the bast fibers have a mean length greater than 4 mm.

DETAILED DESCRIPTION OF INVENTION

A water dispersible nonwoven substrate formed of a majority of individualized fibers which are substantially straight, plant-based, and substantially pectin-free and have a mean length greater than 4 mm is described. In another aspect, the water dispersible nonwoven substrate comprises a majority of fibers that are non-cotton, plant-based, and substantially pectin-free and have a mean length greater than 4 mm. Yet, in another aspect, the water dispersible nonwoven substrate comprises a majority of individualized fibers which are substantially straight, plant-based, and have a mean length greater than 6 mm.

The water dispersible nonwoven substrate can be a variety of products, including, but not limited to, a tissue or a wipe. The tissue can be a pre-moistened tissue. Further, the wipe can be a wet wipe, for example a personal care wet wipe, comprising a wetting composition. The water dispersible nonwoven substrate of the present invention possesses sufficient wet tensile strength for use as a pre-moistened tissue or wet wipe. Despite the wet tensile strength, the nonwoven substrate substantially disperses into smaller pieces and individual fibers in a relatively short time under immersion and mild agitation in water, such as being present in a standard septic tank or sanitary system. The nonwoven substrate's ability to disperse under mild agitation in water is a function of the fiber composition. Further, the water dispersible nonwoven substrate is comprised of natural fibers that can readily biodegrade. The ability to biodegrade and disperse in a septic tank or sanitary system prevents the tissue or wipe from clogging up sewage lines and screens at sewage treatment plants. Thus, the water dispersible nonwoven substrate of the present invention can be used for a variety of application. The water dispersible nonwoven tissue or wipe can then be flushed down a toilet after a single use.

As used herein, the term "plant-based fiber" means a fiber produced by and extracted from a plant as opposed to man-made fibers formed from regenerated cellulose. As used herein, the term "nonwoven" means a web, fabric, or substrate having a structure of individual fibers or threads which are randomly interlaid, but not in an identifiable manner as in the case of a knitted or woven fabric. Examples of suitable nonwoven substrates include, but are not limited to, bonded carded webs, airlaid webs, coform webs, hydraulically entangled webs, and so forth.

As used herein, the term "wipe" means a type of nonwoven article suitable for cleansing, disinfecting, applying a compound, or removing a compound.

As used herein, the term "flushable" means the ability of a material, when flushed, to clear the toilet, drain lines, and screens leading to the municipal wastewater conveyance system.

As used herein, the term "dispersible" means the ability of a material to readily break apart in water. In particular, the term "dispersible" means the ability of a material to readily break apart due to the physical forces encountered during flushing in a common toilet, conveyance in a common wastewater system, and processing in a common treatment system.

The term "basis weight" as used herein means the quantity by weight over a given area. The units of measure include grams per square meter (gsm).

As used herein, the term "tensile strength" means the strength of the nonwoven substrate. Tensile strength can be measured in the cross machine direction (CD) or machine direction (MD). The units of tensile strength include grams/inch (g/in).

A class of fibers which are utilized in the present invention are individualized bast fibers. Bast fibers are extracted from, but not limited to, flax, hemp, jute, ramie, nettle, Spanish broom, kenaf plants. The aforementioned individualized bast fibers can be employed in any combination.

Individualized bast fibers are typically straight and are substantially pectin free. For example, individualized bast fibers have less than 10% by weight of the pectin content of the naturally occurring fibers from which the substantially pectin-free fibers are derived. In another aspect, individualized bast fibers have less than 15% by weight of the pectin content of the naturally occurring fibers from which the substantially pectin-free fibers are derived. Still, in another aspect, individualized bast fibers have less than 20% by weight of the pectin content of the naturally occurring fibers from which the substantially pectin-free fibers are derived.

In one aspect, the nonwoven substrate comprises about 50 weight percent (wt. %) to about 100 wt. % bast fibers, based upon total fiber weight. In another aspect, the nonwoven substrate comprises about 60 wt. % to about 95 wt. % bast fibers, based upon total fiber weight. Yet, in another aspect, the nonwoven substrate comprises between about 75 wt. % to about 90 wt. % bast fibers, based upon total fiber weight. Still yet, in another aspect, the nonwoven substrate comprises between about 80 wt. % to about 100 wt. % bast fibers, based upon total fiber weight.

In one aspect, the nonwoven substrate comprises about 85 wt. % bast fibers and about 15 wt. % regenerated cellulose fibers, based upon total fiber weight. In another aspect, the nonwoven substrate comprises between about 75 wt. % to about 90 wt. % bast fibers and about 25 wt. % to about 10 wt. % regenerated cellulose fibers, based upon total fiber weight. Yet, in another aspect, the nonwoven substrate comprises about 70 wt. % bast fibers and about 30 wt. % regenerated cellulose fibers, based upon total fiber weight.

Examples of regenerated cellulose include, but are not limited to, rayon, lyocell, (e.g., TENCEL®), Viscose®, or any combination thereof. TENCEL® and Viscose® are commercially available from Lenzing Aktiengesellschaft, Lenzing, Austria.

Typically, individualized bast fibers have a mean length in a range between about 4 to 40 mm depending on the characteristics of the particular bast fibers and the cut length of the plant stalks prior to chemical processing. In one aspect, the individualized bast fibers have a mean length of at least 4 mm, at least 6 mm, at least 8 mm, and at least 10 mm. In another aspect, the individualized bast fibers have a mean length greater than 12 mm.

The nonwoven substrate can be formed of a majority of fibers comprising individual bast fibers with less than 10% by weight of the pectin content of the naturally occurring bundled bast fiber from which the individual bast fibers are derived. In another aspect, the individual bast fibers comprise less than 20% by weight of the pectin content of the naturally occurring bundled bast fiber. Moreover, such bast fibers have a mean length greater than 12 mm.

The nonwoven substrate can also comprise staple fibers derived from one or more source. Staple fibers include, but are not limited to, cellulosic fibers and thermoplastic fibers. An example of a cellulosic staple fiber comprises rayon. Thermoplastic fibers include the conventional polymeric fibers utilized in the nonwoven industry. Such fibers are formed from polymers which include, but are not limited to, a polyester such as polyethylene terephthalate; a nylon; a polyamide; a polyolefin such as polypropylene or polyethylene; a blend of two or more of a polyester, a nylon, a polyamide, or a polyolefin; a bi-component composite of any two of a polyester, a nylon, a polyamide, or a polyolefin; and the like. An example of a bi-component composite fiber includes, but is not limited to, a fiber having a core of one polymer and a sheath comprising a polymer different from the core polymer which completely, substantially, or partially encloses the core.

The water dispersible nonwoven substrate can include any natural or cellulose-based fibers, such as those derived from wood pulp, synthetic cellulose-based fibers, or any mixture thereof. Examples of cellulose fibers include, but are not limited to, digested fibers, such as kraft fibers, kraft digested fibers, pre-hydrolyzed kraft fibers, pre-hydrolyzed kraft digested fibers, soda fibers, sulfite fibers, and chemi-thermal mechanical and thermo-mechanical treated fibers derived from softwood, hardwood or cotton linters. Non-limiting examples of cellulose fibers suitable for use in this invention include the cellulose fibers derived from softwoods, such as pines, firs, and spruces.

The nonwoven substrate can include wood pulp. Examples of wood pulp include, but are not limited to, commercially available bright fluff pulp, such as southern softwood fluff pulp, northern softwood sulfite pulp, or hardwood pulp (e.g., eucalyptus).

The individual bast fibers are formed into an unbounded web in the wet or dry state. In one aspect, the web is formed by a method employing a mechanical card. In another aspect, the web is formed by a method employing a combination of a mechanical card and a forced air stream. The dry web can be bonded by hydroentangling, or hydroentanglement. In addition, the hydroentangled web can be treated with an aqueous adhesive and exposed to heat to bond and dry the web. Also, the dry web can be bonded by mechanical needle punching and/or passing a heated air stream through the web. Alternatively, the dry web can be bonded by applying an aqueous adhesive to the unbounded web and exposing the web to heat.

Hydroentanglement, also known as spunlacing, to form non-woven fabrics and substrates is well-known in the art. Non-limiting examples of the hydroentangling process are described in Canadian Patent No. 841,938, U.S. Pat. No. 3,485,706, and U.S. Pat. No. 5,958,186. U.S. Pat. Nos. 3,485,706 and 5,958,186, respectively, are incorporated herein in their entirety by reference. Hydroentangling involves forming a fiber web, either wet-laid or dry-laid, and thereafter entangling the fibers by employing very fine water jets under high pressure. For example, a plurality of rows of waterjets is directed towards the fiber web that is disposed on a moving support, such as a wire (mesh). Hydroentangling of the fibers provides distinct hydroemboss patterns, which can create low fiber count zones, facilitate water dispersion, and provide a three dimensional structure. The entangled web is then dried.

In addition to the substantially individualized bast fibers described herein, synthetic or regenerated staple fibers can be mixed with the bast fibers to form the non-woven substrate. Examples of such fibers include, but are not limited to, polymeric fibers formed from polyester, polyamide, polypropylene, rayon, or the like, and pulp fibers. Non-woven substrates in accordance with the present invention can be formed of substantially individualized bast fibers and staple fibers; bast fibers and pulp fibers; and bast fibers, staple fibers, and pulp fibers.

A fiber web comprising substantially individualized bast fibers can be wet-laid or foam-formed in the presence of a dispersion agent. The dispersion agent can either be directly added to the substantially individualized bast fibers in the form of a so-called "fiber finish" or it can be added to the water system in a wet-laying or foam-forming process. The addition of a suitable dispersion agent assists in providing a good formation, i.e, substantially uniform fiber dispersion, of the substantially individualized bast fibers. The dispersion agent can be of many different types, which provide a suitable dispersion effect on the substantially individualized bast fibers or any mixture of such bast fibers with staple fibers and/or pulp fibers. A non-limiting example of a dispersion agent is a mixture of 75% bis(hydrogenatedtallowalkyl)dimethyl ammonium chloride and 25% propyleneglycol. The addition ought to be within the range of 0.01-0.1 wt. %.

During foam-forming the fibers are dispersed in a foamed liquid containing a foam-forming surfactant and water, whereafter the fiber dispersion is dewatered on a support, e.g., a wire (mesh), in the same way as with wet-laying. After the fiber web is formed, the fiber web is subjected to hydroentanglement with an energy flux of about 23,000 foot-pounds per square inch per second or higher. The hydroentanglement is carried out using conventional techniques and with equipment supplied by machine manufacturers. After hydroentanglement, the material is pressed and dried and, optionally, wound onto a roll. The ready material is then converted in a known way to a suitable format and then packed.

As stated above, in one aspect, nonwoven substrates in accordance with the present invention comprise a majority fiber content that is individualized bast fibers. Naturally occurring bundled bast fibers are chemically treated to remove the pectin holding the bundles together and separate the naturally occurring fibers into individual bast fibers. Pectin acts as a natural glue which holds the individual bast fibers in the bundle. By removing the pectin and separating the individual bast fibers, the individualized bast fibers can be formed into a web while in a dry state prior to subsequent bonding by suitable means to form a nonwoven textile substrate.

Naturally occurring bast fibers, for example from the flax plant, comprise bast fiber bundles, or stacks of small individual flax bast fibers. After pectin removal from the flax bast fiber bundles, the fibers become individualized, which are smooth and elongated. In addition, individual bast fibers do not have kinks or crimps. Use of such fibers to produce a water dispersible nonwoven substrate is novel.

The water dispersible nonwoven substrate can be formed by wet laying or dry-laying methods. Techniques for wet laying fibrous material to form sheets, such as dry lap and paper, are well known in the art. Suitable wet laying techniques include, but are not limited to, hand sheeting and wet laying with paper making machines as described in U.S. Pat. No. 3,301,746, which is incorporated herein in its entirety by reference.

A nonwoven substrate of staple fibers can be formed by a mechanical process known as carding as described in U.S. Pat. No. 797,749, which is incorporated herein in its entirety by reference. The carding process can include an airstream component to randomize the orientation of the staple fibers when they are collected on the forming wire. Typically, the synthetic staple fiber length for a mechanically carded process is in the range of 38-60 mm. Longer lengths are possible depending on the set up of the card. A state of the art mechanical card, such as the Trüzschler-Fliessner EWK-413 card, can run staple fibers having significantly shorter length than the 38 mm noted above. Older card designs may require longer fiber length to achieve good formation and stable operation.

Another common dry web forming process is air-laid or air-forming. This process employs only air flow, gravity, and centripetal force to deposit a stream of fibers onto a moving forming wire that conveys the fiber web to a web bonding process. Air-laid processes are described in U.S. Pat. Nos. 4,014,635 and 4,640,810, both of which are incorporated herein in their entirety by reference. The air-laid process is effective at forming a uniform web of short fibers, e.g., typically less than 6 mm long, with low fiber to fiber cohesion and low potential for generating static. The dominant fiber utilized in these air driven processes is wood pulp, which can be processed at high throughput owing to its short length of 3 mm or less. Pulp-based air-formed nonwoven webs frequently incorporate 10 to 20% of 4 to 6 mm long thermoplastic fibers that melt and bond the air-laid web together when the air-formed web is passed through ovens. It is possible to air-form a layer of 100% thermoplastic fiber in conjunction with a pulp-based layer, however, the fiber throughput rate declines significantly with increasing fiber length. Typically, such fiber lengths above 12 mm are commercially impractical.

It is possible to use a mechanical means such as a mechanical carding process used for staple fibers to form full length, dry individualized bast fibers into a randomly arrayed fiber web that can then be transferred to a web bonding process to create a bast fiber based nonwoven substrate. This aspect is unique in that individual bast fibers, particularly those from the flax or hemp plants, do not have physical dimensions that are characteristic of a cardable staple fiber.

Naturally occurring bundled bast fibers first are chemically treated to substantially remove pectin and form substantially pectin free, individualized fibers. Dry, individualized fibers can be incorporated into fiber bales. The fiber bales are separated in a bale opener and moved into a fiber accumulator. The accumulated fibers can be air-conveyed through a feed chute and then deposited as a fiber feed mat onto a forming wire. The air-conveyed process randomizes the orientation of the fibers when they are collected on the forming wire. The fiber feed mat is fed through a fiber feed roll into the fiber carding equipment, which further separates the fibers into individualized, carded fibers. The fiber doffing roll transfers the carded fibers back onto the forming wire to form the fiber web. The fiber web can then be transferred to web bonding equipment, such as thermal bonding equipment, which is discussed below, to form the nonwoven substrate. The dry web can be bonded by hydroentangling, as discussed above. In addition, the hydroentangled web can be treated with an aqueous adhesive and exposed to heat to bond and dry the web. Also, the dry web can be bonded by mechanical needle punching and/or passing a heated air stream through the web. Alternatively, the dry web can be bonded by applying an aqueous adhesive to the unbounded web and exposing the web to heat.

A typical cardable staple fiber is 38 to 60 mm in length and has 5-10 crimps per inch of fiber length. The crimp in each fiber provides fiber-to-fiber cohesion. The combination of length and crimp gives the unbounded fiber web sufficient strength to allow web transfer between successive rollers in the carding equipment and to be transferred from the card, to the collection wire, and then to bonding equipment, without a break in the web. In contrast, individualized bast fibers may have a length of only 20-25 mm or less and, more significantly, are straight fibers with no natural or mechanically induced crimps to facilitate fiber-to-fiber cohesion. For example, cotton fiber has a natural twist that generates high fiber-to-fiber cohesion. Individualized bast fibers are void of a natural twist. The artificial crimp applied to man-made fiber is an effort to mimic the fiber-to-fiber cohesion effect of the natural twist of cotton fiber. The fiber length and low fiber cohesion of individual bast fibers, according to conventional wisdom, renders them poor candidates for a dry web forming process such as carding. In addition, the natural fiber length of 20-25 mm is, however, too long to be processed at 100% concentration by web forming processes that are driven entirely by air as described respectively in U.S. Pat. Nos. 4,014,635; 4,640,810; and 5,958,186. Nonetheless, in accordance with the present invention, a dry web forming process utilizing carding can be employed to produce a nonwoven substrate comprising a majority of individualized bast fibers.

Thermal bonding is also referred to as calendar bonding, point bonding, or pattern bonding, and optionally, can be used to bond a fiber web to form a nonwoven substrate. Thermal bonding can also incorporate a pattern into the substrate. Thermal bonding is described in PCT International Publication No. WO/2005/025865, which is incorporated herein by reference in its entirety. Thermal bonding requires incorporation of thermoplastic fibers into the fiber web. Examples of thermoplastic fibers are discussed above. In thermal bonding, the fiber web is bonded under pressure by passing through heated calendar rolls, which can be embossed with a pattern that transfers to the surface of the fiber web. During thermal bonding, the calendar rolls are heated to a temperature at least between the glass transition temperature ($T_g$) and the melting temperature ($T_m$) of the thermoplastic material.

PCT International Publication No. WO 2007/140578, which is incorporated herein in its entirety by reference, describes a pectin removal technology that produces individualized hemp and flax fiber for application in the woven textile industry. Although this individualized bast fiber is straight, it has fineness similar to cotton and has a length of at least 20 mm. As discussed above, individualized bast fibers can be spun into threads and yarns as a precursor to woven textile production. The process to remove pectin described in WO 2007/140578 can be employed with the present invention.

The naturally occurring bundled bast fibers and the individualized bast fibers utilized in the present invention, in addition to visual and tactile inspection, can be distinguished by quantified measuring of the relative amounts of pectin present in the bundled versus the individualized bast fibers. A chemical test has been developed to make this relative quantification, which is based on the method described in WO 2007/140578. The test procedure is as follows:

Approximately 30 mg of fiber is exposed to 20 µL of Novozyme Pectinase from *Aspergillus niger* (50× dilution) in 800 µL of a 100 mM sodium citrate buffer that is adjusted to pH 4.5 with hydrochloric acid. The solution is heated to 40° C. for 1 hour. After heating, 50 µL of the liquid solution is removed and added to 1 mL of 10 mM sodium hydroxide. A 3.0 mL aliquot of a 0.5% solution of 4-hydroxy-benzhydrazide (prepared as a 5% solution in 0.5 M hydrochloric acid and diluted with 0.5 M sodium hydroxide to give a 0.5% solution) is added to the solution which is then heated in boiling water for 5 minutes. After cooling, the absorbance of the mixture is measured at 410 nm.

Standards of galacturonic acid are prepared in water, and 50 µL of these solutions are added to 1 mL aliquots of 10 mM sodium hydroxide. Colorimetric analysis of the reducing sugar is followed in the same manner as above.

Table 1 reports the results of a test in terms of the percentage of reduced sugar extracted from the fibers into an aqueous solution. The reduced sugar is pectin in its extracted form. Therefore, the relative fraction of reduced sugar in the aqueous solution correlates with the relative fraction of pectin attached to the bast fibers prior to the extraction test. As indicated in Table 1, individualized bast fibers after enzyme processing have less than 0.1% reduced sugar.

TABLE 1

Relative reduced sugar/pectin content of bast fibers before and after enzymatic treatment

|  | Reduced Sugar Percentage (%)* |
| --- | --- |
| Flax bast fiber bundles before enzyme processing | 1.1 |
| Individualized flax bast fibers after enzyme processing | Less Than 0.1 |

*Reduced sugar extraction is a proportional indicator for pectin content

The nonwoven substrate, either in the form of a tissue or wet wipe, as disclosed herein, can be tailored to provide sufficient in-use wet tensile strength and dispersibility. The nonwoven substrate can be made to be usable without breaking or tearing during use and to provide problem-free disposal once disposed in a household sanitation system.

The total basis weight of the nonwoven substrate, which can include a single layer or multiple layers of nonwoven material in the final tissue or wet wipe product, is in the range between about 10 gsm to about 500 gsm. In another aspect, the total basis weight of the nonwoven substrate is in a range between about 100 gsm to about 300 gsm. Yet, in another aspect, the total basis weight of the nonwoven substrate is in a range between about 75 gsm to about 200 gsm.

In-use wet tensile and residual soak tensile measurements can be measured using a pneumatic grip gauge separation of 5.1 centimeters (cm) and a crosshead speed of 30.1 centimeters/minute (cm/min) as described in U.S. Pat. No. 8,133,825, which is incorporated herein in its entirety by reference. As used herein, in-use wet tensile strength refers to the tensile strength of the nonwoven substrate after being pre-moistened with a wetting composition. As used herein, residual soak tensile measurements refer to the tensile strength of the nonwoven substrate after being immersed in water for the indicated period of time.

The nonwoven substrate has an in-use wet tensile strength in a range between about 100 grams/inch (g/in) to about 1000 g/in. In one aspect, the nonwoven substrate has an in-use wet tensile strength in a range between about 200 g/in to about 800 g/in. In another aspect, the nonwoven substrate has an in-use wet tensile strength in a range between about 300 g/in to about 600 g/in. Still yet, in another aspect, the nonwoven substrate has an in-use wet tensile strength in a range between about 350 g/in to about 550 g/in.

Water dispersibility of the nonwoven substrate can be measured by the method described in U.S. Patent Publication No. 2012/0144611, which is incorporated herein in its entirety by reference. Briefly, the INDA Guidelines FG 511.2 Dispersibility Tipping Tube Test can be used to assess the dispersibility or physical breakup of a flushable product during its transport through household and municipal conveyance systems (e.g., sewer pipe, pumps and lift stations). This test assesses the rate and extent of disintegration of samples by turbulent water via a capped tube that is tipped up and down.

A 1 L graduated cylinder is used to deliver 700 mL of room temperature tap water into a clear plastic acrylic tube measuring 500 mm (19.7 in) in height, with an inside diameter of 73 mm (2.9 in). Each sample in dropped into the tube and allowed to remain in contact with the water for 30 seconds. The top of the plastic tube is sealed with a water tight screw cap fitted with a rubber seal. The tube, initially in a vertical position, is then rotated 180 degrees in a counter clockwise direction (in approximately 1 s) and stopped (for approximately 1 s), then rotated another 180 degrees in a clockwise direction (in approximately 1 s) and stopped (for approximately 1 s). This represents 1 cycle. The test was stopped after 240 cycles.

The contents in the tube are then quickly poured over two screens arranged from top to bottom in descending order: 12 mm and 1.5 mm (diameter opening). A hand held showerhead spray nozzle is held approximately 10-15 cm above the sieve, and the material is gently rinsed through the nested screens for 2 min at a flow rate of 4 L/min (1 gal/min). The flow rate is assessed by measuring the time it takes to fill a 4 L beaker. After the two minutes of rinsing, the top screen is removed.

After rinsing is complete, the retained material is removed from each of the screens, and the 12 mm sieve retained material is placed upon a separate labeled and tared aluminum weigh pan. The pan is placed into a drying oven for at least 12 hours at 105±3 degrees Celsius until the sample is dry. The dried samples are then cooled in a desiccator. After the samples are dry, their mass is determined. The retained fraction and the percentage of disintegration are calculated based on the initial starting mass of the test material. A high retained percent on the screen correlates with a lower water dispersibility.

The water dispersible nonwoven substrate of the present invention can be incorporated into a variety of products. Non-limiting examples of products include tissues, e.g., facial tissues and bath tissues, wipers (or wipes), such as wet wipers, dry wipers, or impregnated wipers, which include personal care wipers, household cleaning wipers, and dusting wipers. Personal care wipers can be impregnated with, e.g., emollients, humectants, fragrances, and the like. Household cleaning wipers or hard surface cleaning wipers can be impregnated with, e.g., surfactants (for example, quaternary amines), peroxides, chlorine, solvents, chelating agents, antimicrobials, fragrances, and the like. Dusting wipers can be impregnated with, e.g., oils.

Various types of wipers include baby wipes, cosmetic wipes, perinea wipes, disposable washcloths, household cleaning wipes, such as kitchen wipes, bath wipes, or hard surface wipes, disinfecting and germ removal wipes, specialty cleaning wipes, such as glass wipes, mirror wipes, leather wipes, electronics wipes, lens wipes, or polishing wipes, medical cleaning wipes, disinfecting wipes, and the like.

As mentioned above, the nonwoven substrate can be a tissue or a wet wipe. The tissue or wet wipe can be pre-moistened with a wetting composition, which can include at least one additive. The wetting composition can be any solution, including, but not limited to, an aqueous solution comprising at least one additive. Non-limiting examples of suitable additives are provided below. The wetting composition can be disposed on or impregnated within the nonwoven substrate by any method. Examples of such methods include, but are not limited to, soaking the nonwoven substrate in the wetting composition and spraying the wetting composition onto the nonwoven substrate.

Relative to the weight of the dry nonwoven substrate, the nonwoven substrate comprises between about 10% to about 400% of the wetting composition. In one aspect, the nonwoven substrate comprises between about 100% to about 300% of the wetting composition, relative to the weight of the dry nonwoven substrate. In another aspect, the nonwoven substrate comprises between about 180% to about 240% of the wetting composition, relative to the dry weight of the nonwoven substrate.

As indicated above, a variety of additives can be employed with the nonwoven substrate products described herein. Suitable additives include, but are not limited to: skin-care additives; odor control agents; detackifying agents if a binder is present in the non-woven substrate to reduce the tackiness of the binder; particulates; antimicrobial agents; preservatives; wetting agents and cleaning agents such as detergents, surfactants, and some silicones; emollients; surface feel modifiers for improved tactile sensation (e.g., lubricity) on the skin; fragrance; fragrance solubilizers; opacifiers; fluorescent whitening agents; UV absorbers; pharmaceuticals; and pH control agents, such as malic acid or potassium hydroxide.

Skin-care additives provide one or more benefits to the user, such as a reduction in the probability of having diaper rash and/or other skin damage caused by fecal enzymes. These enzymes, particularly trypsin, chymotrypsin and elastase, are proteolytic enzymes produced in the gastrointestinal tract to digest food. In infants, for example, the feces tend to be watery and contain, among other materials, bacteria, and some amounts of undegraded digestive enzymes. These enzymes, if they remain in contact with the skin for any appreciable period of time, may cause an irritation that is uncomfortable in itself and can predispose the skin to infection by microorganisms. As a countermeasure, skin-care additives include, but are not limited to, the enzyme inhibitors and sequestrants. The wetting composition can contain less than about 5 weight percent of skin-care additives based on the total weight of the wetting composition. More specifically, the wetting composition can contain from about 0.01 weight percent to about 2 weight percent of skin-care additives. Even more specifically, the wetting composition can contain from about 0.01 weight percent to about 0.05 weight percent of skin-care additives.

A variety of skin-care additives can be added to the wetting composition and the pre-moistened wipes of the present invention or included therein. For example, skin-care additives in the form of particles can be added to serve as fecal enzyme inhibitors, offering potential benefits in the reduction of diaper rash and skin damage caused by fecal enzymes. U.S. Pat. No. 6,051,749, which is incorporated herein by reference in its entirety, discloses organophilic clays in a woven or nonwoven web described as being useful for inhibiting fecal enzymes. Such materials can be used in the present invention, including reaction products of a long chain organic quaternary ammonium compound with one or more of the following clays: montmorillonite, bentonite, beidellite, hectorite, saponite, and stevensite.

Other known enzyme inhibitors and sequestrants can be used as skin-care additives in the wetting composition of the present invention, including those that inhibit trypsin and other digestive or fecal enzymes, and inhibitors for urease. For example, enzyme inhibitors and anti-microbial agents may be used to prevent the formation of odors in body fluids. For example, urease inhibitors, which are also said to play a role in odor absorption, are disclosed by T. Trinh in PCT International Publication No. 98/26808, which is incorporated herein by reference in its entirety. Such inhibitors can be incorporated into the wetting composition and the pre-moistened wipes of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride.

Other salts known to have urease inhibition properties include ferric and aluminum salts, such as the nitrates, and bismuth salts. Other urease inhibitors include hydroxamic acid and its derivatives; thiourea; hydroxylamine; salts of phytic acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosphoramidates without substitution on the nitrogen; boric acid and/or its salts, including especially, borax, and/or organic boron acid compounds; the compounds disclosed in European Patent Application 408,199; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; behenic acid; N,N-dihalo-2-imidazolidinones; N-halo-2-oxazolidinones; thio- and/or acyl-phosphoryltnamide and/or substituted derivatives thereof; thiopyridine-N-oxides, thiopyridines, and thiopyrimidines; oxidized sulfur derivatives of diaminophosphinyl compounds; cyclo triphosphazatriene derivatives; bromo-nitro compounds; S-aryl and/or alkyl diamidophosphorothiolates; diaminophosphinyl derivatives; mono- and/or polyphosphorodiamide; alkoxy-1, 2-benzothaizin compounds; ortho-diaminophosphinyl derivatives of oximes; 5-substituted-benzoxathiol-2-ones; N(diammophosphinyl)arylcarboxamides; and the like.

Many other skin-care additives may be incorporated into the wetting composition and pre-moistened wipes of the present invention, including, but not limited to, sun blocking agents and UV absorbers, acne treatments, pharmaceuticals, baking soda (including encapsulated forms thereof), vitamins and their derivatives such as Vitamins A or E, botanicals such as witch hazel extract and aloe vera, allantoin, emollients, disinfectants, hydroxy acids for wrinkle control or anti-aging effects, sunscreens, tanning promoters, skin lighteners, deodorants and anti-perspirants, ceramides for skin benefits and other uses, astringents, moisturizers, nail polish removers, insect repellants, antioxidants, antiseptics, anti-inflammatory agents and the like. Useful materials for skin care and other benefits are listed in McCutcheon's 1999, Vol. 2: Functional Materials, MC Publishing Company, Glen Rock, N.J. Many useful botanicals for skin care are provided by Active Organics, Lewisville, Tex.

Suitable odor control additives for use in the wetting composition and pre-moistened wipes of the present invention include, but are not limited to, zinc salts; talc powder; encapsulated perfumes (including microcapsules, macrocapsules, and perfume encapsulated in liposomes, vessicles, or microemulsions); chelants, such as ethylenediamine tetraacetic acid; zeolites; activated silica; activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites; triclosan; kieselguhr; and mixtures thereof. In addition to controlling odor from the body or body wastes, odor control strategies can also be employed to mask or control any odor of the treated substrate. Typically, the wetting composition contains less than about 5 weight percent of odor control additives based on the total weight of the wetting composition. In another aspect, the wetting composition contains from about 0.01 weight percent to about 2 weight percent of odor control additives. Yet, in another aspect, the wetting composition contains from about 0.03 weight percent to about 1 weight percent of odor control additives.

In one embodiment of the present invention, the wetting composition and/or pre-moistened wipes comprise derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product.

Principles for the application of chitosan or chitin derivatives to nonwoven webs and cellulosic fibers are described by S. Lee et al. in "Antimicrobial and Blood Repellent Finishes for Cotton and Nonwoven Fabrics Based on Chitosan and Fluoropolymers," Textile Research Journal, 69(2); 104-112, February 1999.

If a binder is employed in the non-woven substrate, detackifying agents can be used in the wetting composition to reduce the tackiness of the binder. Suitable detackifiers include any substance known in the art to reduce tack between two adjacent fibrous sheets treated with an adhesive-like polymer or any substance capable of reducing the tacky feel of an adhesive-like polymer on the skin. Detackifiers can be applied as solid particles in dry form, as a suspension or as a slurry of particles. Deposition can be by spray, coating, electrostatic deposition, impingement, filtration (i.e., a pressure differential drives a particle-laden gas phase through the substrate, depositing particles by a filtration mechanism), and the like, and can be applied uniformly on one or more surfaces of the substrate or may be applied in a pattern (e.g., repeating or random patterns) over a portion of the surface or surfaces of the substrate. The detackifier can be present throughout the thickness of the substrate, but may be concentrated at one or both surfaces, and may be substantially only present on one or both surfaces of the substrate.

Specific detackifiers include, but are not limited to, powders, such as talc powder, calcium carbonate, mica; starches, such as corn starch; lycopodium powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins and thermoplastics, waxes, debonding agents known in the paper industry including compounds having alkyl side chains such as those having 16 or more carbons, and the like. Compounds used as release agents for molds and candle making may also be considered, as well as, dry lubricants and fluorinated release agents.

The wetting composition of the present invention can be further modified by the addition of solid particulates or microparticulates. Suitable particulates include, but are not limited to, mica, silica, alumina, calcium carbonate, kaolin, talc, and zeolites. The particulates can be treated with stearic acid or other additives to enhance the attraction or bridging of the particulates to the binder system, if desired. Also, two-component microparticulate systems, commonly used as retention aids in the papermaking industry, can be used. Such two-component microparticulate systems generally comprise a colloidal particle phase, such as silica particles, and a water-soluble cationic polymer for bridging the particles to the fibers of the web to be formed. The presence of particulates in the wetting composition can serve one or more useful functions, such as (1) increasing the opacity of the pre-moistened wipes; (2) modifying the rheology or reducing the tackiness of the pre-moistened wipe; (3) improving the tactile properties of the wipe; or (4) delivering desired agents to the skin via a particulate carrier, such as a porous carrier or a microcapsule. Typically, the wetting composition contains less than about 25 weight percent of particulate based on the total weight of the wetting composition. In another aspect, the wetting composition contains from about 0.05 weight percent to about 10 weight percent of microparticulate. Yet, in another aspect, the wetting composition contains from about 0.1 weight percent to about 5 weight percent of microparticulate.

Microcapsules and other delivery vehicles can also be used in the wetting composition of the present invention to provide skin-care agents; medications; comfort promoting agents, such as eucalyptus; perfumes; skin care agents; odor control additives; vitamins; powders; and other additives to the skin of the user. For example, the wetting composition can contain up to about 25 weight percent of microcapsules or other delivery vehicles based on the total weight of the wetting composition. In another aspect, the wetting composition can contain from about 0.05 weight percent to about 10 weight percent of microcapsules or other delivery vehicles. Yet, in another aspect, the wetting composition can contain from about 0.2 weight percent to about 5.0 weight percent of microcapsules or other delivery vehicles.

Microcapsules and other delivery vehicles are well known in the art. For example, POLY-PORE® E200 (Chemdal Corp., Arlington Heights, EL), is a delivery agent comprising soft, hollow spheres that can contain an additive at over 10 times the weight of the delivery vehicle. Known additives reported to have been used with POLY-PORE® E200 include, but are not limited to, benzoyl peroxide, salicylic acid, retinol, retinol palmitate, octyl methoxycinnamate, tocopherol, silicone compounds (DC 435), and mineral oil. Another delivery vehicle which can be employed with non-woven fabric is a sponge-like material marketed as POLY-PORE® L200, which is reported to have been used with silicone (DC 435) and mineral oil. Other known delivery systems include cyclodextrins and their derivatives, liposomes, polymeric sponges, and spray-dried starch. Additives present in microcapsules are isolated from the environment and the other agents in the wetting composition until the wipe is applied to the skin, whereupon the microcapsules break and deliver their load to the skin or other surfaces.

The wetting composition of the present invention can contain preservatives and/or anti-microbial agents. Several preservatives and/or anti-microbial agents useful in the present invention include, but are not limited to, Mackstat H 66 (available from McIntyre Group, Chicago, Ill.), DMDM hydantoin (e.g., Glydant Plus™, Lonza, Inc., Fair Lawn, N.J.), iodopropynyl butylcarbamate, Kathon (Rohm and Hass, Philadelphia, Pa.), methylparaben, propylparaben, 2-bromo-2-nitropropane-1,3-diol, benzoic acid, and the like. Typically, the wetting composition contains less than about 2 weight percent on an active basis of preservatives and/or antimicrobial agents based on the total weight of the wetting composition. In another aspect, the wetting composition contains from about 0.01 weight percent to about 1 weight percent of preservatives and/or anti-microbial agents. Yet, in another aspect, the wetting composition contains from about 0.01 weight percent to about 0.5 weight percent of preservatives and/or anti-microbial agents.

A variety of wetting agents and/or cleaning agents can be used in the wetting composition of the present invention. Suitable wetting agents and/or cleaning agents include, but are not limited to, detergents and nonionic, amphoteric, and anionic surfactants, especially amino acid-based surfactants. Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants. One function of the surfactant is to improve wetting of the dry substrate with the wetting composition. Another function of the surfactant can be to disperse bathroom soils when the pre-moistened wipe contacts a soiled area and to enhance their absorption into the substrate. The surfactant can further assist in make-up removal, general personal cleansing, hard surface cleansing, odor control, and the like.

One commercial example of an amino-acid based surfactant is acylglutamate, marketed under the Amisoft name by Ajinomoto Corp., Tokyo, Japan. Typically, the wetting composition contains less than about 3 weight percent of wetting agents and/or cleaning agents based on the total weight of the wetting composition. In another aspect, the wetting composition contains from about 0.01 weight percent to about 2 weight percent of wetting agents and/or cleaning agents. Yet, in another aspect, the wetting composition contains from about 0.1 weight percent to about 0.5 weight percent of wetting agents and/or cleaning agents.

In addition to amino-acid based surfactants, a wide variety of surfactants can be used in the present invention. Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic surfactants (BASF Wyandotte Corp.), such as those in which the polyoxypropylene ether has a molecular weight of about 1500-3000 and the polyoxyethylene content is about 35-55% of the molecule by weight, i.e. Pluronic L-62.

Other useful nonionic surfactants include, but are not limited to, the condensation products of C8-C22 alkyl alcohols with 2-50 moles of ethylene oxide per mole of alcohol. Examples of compounds of this type include commercially-available Poly-Tergent SLF series from Olin Chemicals or the TERGITOL® series from Union Carbide, i.e. TERGITOL® 25-L-7, which is formed by condensing about 7 moles of ethylene oxide with a C12-C15 alkanol.

Other nonionic surfactants, which can be employed in the wetting composition of the present invention, include the ethylene oxide esters of C6-C12 alkyl phenols such as (nonylphenoxy)polyoxyethylene ether. Particularly useful are the esters prepared by condensing about 8-12 moles of ethylene oxide with nonylphenol, i.e. the IGEPAL® CO series (GAF Corp.). Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Corning Corp as Dow Corning 190 and 193 surfactants (CTFA name: dimethicone copolyol). These surfactants function, with or without any volatile silicones used as solvents, to control foaming produced by the other surfactants, and also impart a shine to metallic, ceramic, and glass surfaces.

Anionic surfactants can be used in the wetting compositions of the present invention. Anionic surfactants are useful due to their high detergency include anionic detergent salts having alkyl substituents of 8 to 22 carbon atoms such as the water-soluble higher fatty acid alkali metal soaps, e.g., sodium myristate and sodium palmitate. A preferred class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples available as the Bio-Soft series, i.e. Bio-Soft D-40 (Stepan Chemical Co.).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium C14-C16-alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a C12-C15 n-alkanol, i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toluene sulfonate and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

The wetting composition can further comprise an aqueous microemulsion of silicone particles. For example, U.S. Pat. No. 6,037,407, which is incorporated herein in its entirety by reference, describes organopolysiloxanes in an aqueous microemulsion. Typically, the wetting composition contains less than about 5 weight percent of a microemulsion of silicone particles based on the total weight of the wetting composition. In another aspect, the wetting composition contains from about 0.02 weight percent to about 3 weight percent of a microemulsion of silicone particles. Yet, in another aspect, the wetting composition contains from about 0.02 weight percent to about 0.5 weight percent of a microemulsion of silicone particles.

Silicone emulsions in general can be applied to the pre-moistened wipe by any known coating method. For example, the pre-moistened wipe may be moistened with a wetting composition comprising a water-dispersible or water-miscible, silicone-based component. Further, the wipe can comprise a nonwoven web of fibers having a water-dispersible binder, wherein the web is moistened with a lotion comprising a silicone-based sulfosuccinate. The silicone-based sulfosuccinate provides gentle and effective cleansing without a high level of surfactant. Additionally, the silicone-based sulfosuccinate provides a solubilization function, which prevents precipitation of oil-soluble components, such as fragrance components, vitamin extracts, plant extracts, and essential oils.

In one aspect of the present invention, the wetting composition comprises a silicone copolyol sulfosuccinate, such as disodium dimethicone copolyol sulfosuccinate and diammonium dimethicone copolyolsulfosuccinate. In one aspect, the wetting composition comprises less than about 2 percent by weight of the silicone-based sulfosuccinate, and, in another aspect, from about 0.05 percent to about 0.30 percent by weight of the silicone-based sulfosuccinate.

In another example of a product comprising a silicone emulsions, Dow Corning 9506 powder can be present in the wetting composition. Dow Corning 9506 powder is believed to comprise a dimethicone/vinyldimethicone cross-polymer and is a spherical powder, which is said to be useful in controlling skin oils (see "New Chemical Perspectives," Soap and Cosmetics, Vol. 76, No. 3, March 2000, p. 12). Thus, a water-dispersible wipe, which delivers a powder effective in controlling skin oil, is also within the scope of the present invention. Principles for preparing silicone emulsions are disclosed in WO 97/10100.

The wetting composition of the present invention can contain one or more emollients. Suitable emollients include, but are not limited to, PEG 75 lanolin, methyl gluceth 20 benzoate, C12-C15 alkyl benzoate, ethoxylated cetyl stearyl alcohol, products marketed as Lambent wax WS-L, Lambent WD-F, Cetiol HE (Henkel Corp.), Glucam P20 (Amerchol), Polyox WSR N-10 (Union Carbide), Polyox WSR N-3000 (Union Carbide), Luviquat (BASF), Finsolv SLB 101 (Finetex Corp.), mink oil, allantoin, stearyl alcohol, Estol 1517 (Unichema), and Finsolv SLB 201 (Finetex Corp.).

An emollient can also be applied to a surface of the non-woven fabric prior to or after wetting with the wetting composition. Such an emollient can be insoluble in the wetting composition and can be immobile except when exposed to a force. For example, a petrolatum-based emollient can be applied to one surface in a pattern, after which the other surface is wetted to saturate the wipe. Such a product could provide a cleaning surface and an opposing skin treatment surface.

The emollient composition in such products and other products of the present invention can comprise a plastic or fluid emollient such as one or more liquid hydrocarbons (e.g., petrolatum), mineral oil and the like, vegetable and animal fats (e.g., lanolin, phospholipids and their derivatives) and/or a silicone materials such as one or more alkyl substituted polysiloxane polymers, including the polysiloxane emollients disclosed in U.S. Pat. No. 5,891,126, which is incorporated herein in its entirety by reference. Optionally, a hydrophilic surfactant can be combined with a plastic emollient to improve wettability of the coated surface. In some embodiments of the present invention, it is contemplated that liquid hydrocarbon emollients and/or alkyl substituted polysiloxane polymers may be blended or combined with one or more fatty acid ester emollients derived from fatty acids or fatty alcohols.

In one aspect of the present invention, the emollient material is in the form of an emollient blend. For example, the emollient blend can comprise a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. In another aspect, the emollient blend comprises a combination of liquid hydrocarbons (e.g., petrolatum) with dimethicone or with dimethicone and other alkyl substituted polysiloxane polymers. In some embodiments of the present invention, it is contemplated that blends of liquid hydrocarbon emollients and/or alkyl substituted polysiloxane polymers may be blended with one or more fatty acid ester emollients derived from fatty acids or fatty alcohols. PEG-7 glyceryl cocoate, available as Standamul HE (Henkel Corp., Hoboken, N.J.), can also be considered.

Water-soluble, self-emulsifying emollient oils, which are useful in the present wetting compositions, include the polyoxyalkoxylated lanolins and the polyoxyalkoxylated fatty alcohols, as disclosed in U.S. Pat. No. 4,690,821, which is incorporated herein in its entirety by reference. The polyoxyalkoxy chains comprise mixed propylenoxy and ethyleneoxy units. The lanolin derivatives typically comprise about 20-70 such lower-alkoxy units while the C12-C20 fatty alcohols will be derivatized with about 8-15 lower-alkyl units. One such useful lanolin derivative is Lanexol AWS (PPG-12-PEG-50, Croda, Inc., New York, N.Y.). A useful poly(15-20)C2-C3-alkoxylate is PPG-5-Ceteth-20, known as Procetyl AWS (Croda, Inc.).

Typically, the wetting composition contains less than about 25 weight percent of emollients based on the total weight of the wetting composition. In another aspect, the wetting composition can comprise less than about 5 weight percent emollient, and, in yet another aspect, less than about 2% emollient. Still, in another aspect, the wetting composition can contain from about 0.01 weight percent to about 8 weight percent of emollients. Yet still, in another aspect, the wetting composition can contain from about 0.2 weight percent to about 2 weight percent of emollients.

In one aspect, the wetting composition and/or pre-moistened wipes of the present invention comprise an oil-in-water emulsion comprising an oil phase containing at least one emollient oil and at least one emollient wax stabilizer dispersed in an aqueous phase comprising at least one polyhydric alcohol emollient and at least one organic water-soluble detergent, as disclosed in U.S. Pat. No. 4,559,157, the entirety of which is herein incorporated by reference.

Surface feel modifiers can be employed with the non-woven fabric of the present invention to improve the tactile sensation (e.g., lubricity) of the skin during use of the product. Suitable surface feel modifiers include, but are not limited to, commercial debonders; and softeners, such as the softeners used in the art of tissue making including quaternary ammonium compounds with fatty acid side groups, silicones, waxes, and the like. Exemplary quaternary ammonium compounds with utility as softeners are disclosed in U.S. Pat. Nos. 3,554,862; 4,144,122; 5,573,637; and 4,476,323, the entirety of all of which is herein incorporated by reference. Typically, the wetting composition contains less than about 2 weight percent of surface feel modifiers based on the total weight of the wetting composition. In another aspect, the wetting composition contains from about 0.01 weight percent to about 1 weight percent of surface feel modifiers. Yet, in another aspect, the wetting composition contains from about 0.01 weight percent to about 0.05 weight percent of surface feel modifiers.

A variety of fragrances can be used in the wetting composition of the present invention. Typically, the wetting composition contains less than about 2 weight percent of fragrances based on the total weight of the wetting composition. In another aspect, the wetting composition contains from about 0.01 weight percent to about 1 weight percent of fragrances. Yet, in another aspect, the wetting composition contains from about 0.01 weight percent to about 0.05 weight percent of fragrances.

Further, a variety of fragrance solubilizers can be used in the wetting composition of the present invention. Suitable fragrance solubilizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), Brij 78 and Brij 98 (ICI Surfactants), Arlasolve 200 (ICI Surfactants), Calfax 16L-35 (Pilot Chemical Co.), Capmul POE-S (Abitec Corp.), Finsolv SUBSTANTIAL (Finetex), and the like. Typically, the wetting composition contains less than about 2 weight percent of fragrance solubilizers based on the total weight of the wetting composition. In another aspect, the wetting composition contains from about 0.01 weight percent to about 1 weight percent of fragrance solubilizers. Yet, in another aspect, the wetting composition contains from about 0.01 weight percent to about 0.05 weight percent of fragrance solubilizers.

Opacifers can be employed in the wetting composition. Suitable opacifiers include, but are not limited to, titanium dioxide or other minerals or pigments, and synthetic opacifiers such as REACTOPAQUE® particles (available from Sequa Chemicals, Inc., Chester, S.C.). Typically, the wetting composition contains less than about 2 weight percent of opacifiers based on the total weight of the wetting composition. In another aspect, the wetting composition contains from about 0.01 weight percent to about 1 weight percent of opacifiers. Yet, in another aspect, the wetting composition contains from about 0.01 weight percent to about 0.05 weight percent of opacifiers.

Suitable pH control agents for use in the wetting composition of the present invention include, but are not limited to, malic acid, citric acid, hydrochloric acid, acetic acid, sodium hydroxide, potassium hydroxide, and the like. An appropriate pH range minimizes the amount of skin irritation resulting from the wetting composition on the skin. Typically, the pH range of the wetting composition is from about 3.5 to about 6.5. In another aspect, the pH range of the wetting composition is from about 4 to about 6. Sill, in another aspect, the wetting composition contains less than about 2 weight percent of a pH adjuster based on the total weight of the wetting composition. In another aspect, the wetting composition contains from about 0.01 weight percent to about 1 weight percent of a pH adjuster. Yet, in another aspect, the wetting composition contains from about 0.01 weight percent to about 0.05 weight percent of a pH adjuster.

A variety of wetting compositions, formed from one or more of the above-described components, can be used with the wet wipes of the present invention.

The tissue or wipe can be individually folded and packaged in a moisture proof envelope, or packaged in containers holding any desired number of sheets in a water-tight package. The finished tissues or wipes also can be packaged as a roll of separable sheets in a moisture-proof container, which can hold any desired number of sheets on the roll with a wetting composition applied to the wipes. The roll can be coreless and either hollow or solid. Coreless rolls, including rolls with a hollow center or without a solid center, can be produced with known coreless roll winders, including those available from SRP Industry, Inc. (San Jose, Calif.); Shimizu Manufacturing (Japan), and the devices disclosed in U.S. Pat. No. 4,667,890, which is incorporated herein in its entirety by reference. Solid-wound coreless rolls can offer more product for a given volume and can be adapted for a wide variety of dispensers. The water dispersible nonwoven substrate can be packaged into any impermeable envelopes and storage package for suitable for wet-packaged materials.

EXAMPLES

Example 1

Water dispersible nonwoven substrates in accordance with the present invention were prepared with a blend of 85% depectinated Crailar® flax fibers and 15% Tencel® reconstituted cellulose fibers. The flax fibers had an approximate mean length of 20-25 mm and the reconstituted cellulose fibers had a mean fiber size of 1.7 decitex (dtex; mass in grams per 10,000 meters) and length of 40 mm. The two fibers were uniformly blended and then carded into a web on a Trüzschler EWK-413 Model card. The resulting fiber web was bonded by hydroentangling the fiber web with a series of 6 hydrojets.

Table 2 shows the actual pressure gauge settings on the hydrojets. The production line speed on the hydroentangling wire was 27.5 meters/minute (90.3 feet/minute). An emboss pattern was not applied onto the nonwoven fabric during or after hydroentangling.

TABLE 2

| | Hydrojet process settings | | | | | |
|---|---|---|---|---|---|---|
| | Hydro-jet #1 | Hydro-jet #2 | Hydro-jet #3 | Hydro-jet #4 | Hydro-jet #5 | Hydro-jet #6 |
| Entangling energy (Bars) | 30 | 40 | 35 | 35 | 55 | 55 |

Table 3 shows the calculated amount of cumulative energy imparted to the fibers by the series of six hydrojets. Table 4 shows the hydrojet energy calculation method, and Table 5 shows the units calculated to metric equivalents for the energy calculations.

TABLE 3

| Hydrojet Energy Delivery to Fibers | | |
|---|---|---|
| Total Specific Hydroentangling Energy (SI) | kJ/kg | 1,500 |
| Total Specific Hydroentangling Energy (ENG) | hp-hrs/lb | 0.254 |

TABLE 4

| Specific Energy - Hydroentangling (kilo joules/kilogram) | | | | | | | |
|---|---|---|---|---|---|---|---|
| Inputs | Units | Jet Strip 1 | Jet Strip 2 | Jet Strip 3 | Jet Strip 4 | Jet Strip 5 | Jet Strip 6 |
| Coefficient of discharge, typically .6-.7 | | 0.6 | 0.6 | 0.6 | 0.6 | 0.6 | 0.6 |
| diameter of jet orifice | inch | 0.0055 | 0.0055 | 0.0055 | 0.0055 | 0.0055 | 0.0055 |
| number of orifice rows/strip | | 1 | 1 | 1 | 1 | 1 | 1 |
| orifice spacing | inch c to c | 0.025 | 0.025 | 0.025 | 0.025 | 0.025 | 0.025 |
| numer orifices/inch | #/inch | 40 | 40 | 40 | 40 | 40 | 40 |
| manifold gauge pressure | bar | 30 | 40 | 35 | 35 | 55 | 55 |
| manifold gauge pressure | psi | 435 | 580 | 507.5 | 507.5 | 797.5 | 797.5 |
| density of water | kg/m³ | 1000.00 | 1000.00 | 1000.00 | 1000.00 | 1000.00 | 1000.00 |
| fabric speed | ft/min | 90.3 | 90.3 | 90.3 | 90.3 | 90.3 | 90.3 |
| basis weight of fabric | gsm | 49 | 49 | 49 | 49 | 49 | 49 |

TABLE 5

Units converted to metric equivalents for energy calculations

| Symbol | Definition | Unit | Jet Strip 1 | Jet Strip 2 | Jet Strip 3 |
|---|---|---|---|---|---|
| $C_d$ | Coefficient of discharge, typically 0.6-0.7 | | 0.6 | 0.6 | 0.6 |
| d | diameter of jet orifice | m | 0.0001397 | 0.0001397 | 0.0001397 |
| P | manifold gauge pressure | $N/m^2$ | 2,999,219 | 3,998,959 | 3,499,089 |
| ρ | density of water | $kg/m^3$ | 1000.00 | 1000.00 | 1000.00 |
| N | # of jets per meter | 1/m | 1,575 | 1,575 | 1,575 |
| s | fabric speed | m/sec | 0.46 | 0.46 | 0.46 |
| w | basis weight of fabric | $g/m^2$ | 49.00 | 49.00 | 49.00 |
| SE | specific energy | kJ/kg | 149.6718 | 230.4348 | 188.6080 |
| | Total Specific Energy/kg | kJ/kg | 1,500 | | |
| | Total Specific Energy/lb | hp-hrs/lb | 0.254 | | |
| | Average Jet Velocity | m/sec | 46.47 | 53.66 | 50.19 |
| | flow/orifice | m3/sec | 7.12E-07 | 8.22E-07 | 7.69E-07 |
| | flow/orifice | gal/min | 1.13E-02 | 1.30E-02 | 1.22E-02 |
| | flow/strip | gal/min | 10.84 | 12.52 | 11.71 |
| | Total water flow | gal/min | 76 | | |
| | water flow per inch of width | gal/min | 3.2 | | |

| Symbol | Definition | Unit | Jet Strip 4 | Jet Strip 5 | Jet Strip 6 |
|---|---|---|---|---|---|
| $C_d$ | Coefficient of discharge, typically 0.6-0.7 | | 0.6 | 0.6 | 0.6 |
| d | diameter of jet orifice | m | 0.0001397 | 0.0001397 | 0.0001397 |
| P | manifold gauge pressure | $N/m^2$ | 3,499,089 | 5,498,569 | 5,498,569 |
| ρ | density of water | $kg/m^3$ | 1000.00 | 1000.00 | 1000.00 |
| N | # of jets per meter | 1/m | 1,575 | 1,575 | 1,575 |
| s | fabric speed | m/sec | 0.46 | 0.46 | 0.46 |
| w | basis weight of fabric | $g/m^2$ | 49.00 | 49.00 | 49.00 |
| SE | specific energy | kJ/kg | 188.6080 | 371.5371 | 371.5371 |
| | Total Specific Energy/kg | kJ/kg | | | |
| | Total Specific Energy/lb | hp-hrs/lb | | | |
| | Average Jet Velocity | m/sec | 50.19 | 62.92 | 62.92 |
| | flow/orifice | m3/sec | 7.69E-07 | 9.64E-07 | 9.64E-07 |
| | flow/orifice | gal/min | 1.22E-02 | 1.53E-02 | 1.53E-02 |
| | flow/strip | gal/min | 11.71 | 14.68 | 14.68 |
| | Total water flow | gal/min | | | |
| | water flow per inch of width | gal/min | | | |

Example 2

The physical properties of the water dispersible nonwoven substrates of Example 1 were assessed. The basis weight was measured according to (TAPPI) method TM 194H. Caliper was measured according to INDA method WSP120.1.R4912. Wet and dry tensile were measured according to INDA method WSP 110.4(09). Absorbent Capacity was measured according to INDA method WSP010.1.R3(12). Water dispersibility was measured according to INDA test method FG 511.2.

TABLE 6

Physical properties of the inventive water dispersible wipe substrate

| | Emboss Pattern | Dry Caliper 8 Sheet mils/8 sht | Basis Weight gsm | Dry Tensile Wiper 1 × 4" CD g/1-in Width | Dry Tensile Wiper 1 × 4" MD g/1-in Width | Dry Stretch Wiper 1 × 4" CD % | Dry Stretch Wiper 1 × 4" MD % |
|---|---|---|---|---|---|---|---|
| Test Procedure # | | INDA WSP120.1.R4912 | TAPPI Method TM 194H | INDA WSP 110.4(09) | INDA WSP 110.4(09) | INDA WSP 110.4(09) | INDA WSP 110.4(09) |
| Result | None | 141.75 | 49.06 | 224.56 | 679.31 | 64.34 | 14.84 |

| | | Dry TEA Wiper 1 × 4" CD gm/mm | Dry TEA Wiper 1 × 4" MD gm/mm | Wet MD/CD Tensile Ratio | Wet Tens Wiper 1 × 4-CD g/1-in Width | Wet Tens Wiper 1 × 4-MD g/1-in Width | Tip Tube Mass Loss (%) |
|---|---|---|---|---|---|---|---|
| Test Procedure # | | INDA WSP 110.4(09) | INDA WSP 110.4(09) | N/A | INDA WSP 110.4(09) | INDA WSP 110.4(09) | INDA FG 511.2 |
| Result | | 3.99 | 2.72 | 2.14 | 173.47 | 371.76 | 4.9 |

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A water dispersible nonwoven substrate comprising a majority of individualized bast fibers which are substantially straight, substantially pectin-free, and have a mean length greater than 4 millimeters (mm).

2. The water dispersible nonwoven substrate of claim 1, wherein the nonwoven substrate is impregnated with a wetting composition comprising least one additive.

3. The water dispersible nonwoven substrate of claim 2, wherein the at least one additive is a skin care additive, an odor control additive, a de-tackifying agent, a microparticulate, a microcapsule, a preservative, an anti-bacterial agent, a wetting agent, a cleaning agent, a microemulsion, an emollient, a surface feel modifier, a fragrance, a fragrance solubilizer, an opacifier, or a pH control agent.

4. The water dispersible nonwoven substrate of claim 1, wherein the substantially straight, substantially pectin-free fibers are fibers extracted from flax, hemp, jute, ramie, nettle, Spanish broom, kenaf plants, or any combination thereof.

5. The water dispersible nonwoven substrate of claim 1, wherein the substantially straight, substantially pectin-free fibers have less than 10% by weight of the pectin content of the naturally occurring fibers from which the substantially pectin-free fibers are derived.

6. The water dispersible nonwoven substrate of claim 1, wherein the substantially straight, substantially pectin-free fibers have less than 15% by weight of the pectin content of the naturally occurring fibers from which the substantially pectin-free fibers are derived.

7. The water dispersible nonwoven substrate of claim 1, wherein the substantially straight, substantially pectin-free fibers have less than 20% by weight of the pectin content of the naturally occurring fibers from which the substantially pectin-free fibers are derived.

8. The water dispersible nonwoven substrate of claim 1, wherein the substantially straight, substantially pectin-free fibers having a mean length of at least 5 mm.

9. The water dispersible nonwoven substrate of claim 1, wherein the substantially straight, substantially pectin-free fibers have a mean length of at least 6 mm.

10. The water dispersible nonwoven substrate of claim 1, wherein the substantially straight, substantially pectin-free fibers having a mean length of at least 7 mm.

11. The water dispersible nonwoven substrate of claim 1, wherein the substantially straight, substantially pectin-free fibers have a mean length of at least 8 mm.

12. The water dispersible nonwoven substrate of claim 1, wherein the substantially straight, substantially pectin-free fibers have a mean length greater than 9 mm.

13. The water dispersible nonwoven substrate of claim 1, further comprising crimped or straight staple fibers.

14. The water dispersible nonwoven substrate of claim 1, further comprising crimped or straight man-made cellulosic fibers.

15. The water dispersible nonwoven substrate of claim 1, further comprising regenerated cellulosic fibers.

16. The water dispersible nonwoven substrate of claim 1, further comprising wood pulp fibers.

17. The water dispersible nonwoven substrate of claim 1, wherein the nonwoven substrate has a basis weight in a range between about 10 gsm to about 500 gsm.

18. The water dispersible nonwoven substrate of claim 1, wherein the nonwoven substrate is a wet wipe, a dry wipe, or an impregnated wipe.

19. The water dispersible nonwoven substrate of claim 1, wherein the water dispersible nonwoven substrate is a tissue, a facial tissue, a bath tissue, a baby wipe, a personal care wipe, a personal protective wipe, a cosmetic wipe, a perinea wipe, a disposable washcloth, a kitchen wipe, an automotive wipe, a bath wipe, a hard surface wipe, a cleaning wipe, a disinfecting wipe, a glass wipe, a mirror wipe, a leather wipe, an electronics wipe, a lens wipe, a polishing wipe, a medical cleaning wipe, or a disinfecting wipe.

20. The water dispersible nonwoven substrate of claim 1, wherein the nonwoven substrate is hydroentangled.

21. A method of making the water dispersible nonwoven substrate of claim 1, the method comprising:
chemically treating naturally occurring fibers to substantially remove pectin and form substantially individualized fibers;
forming a fiber web; and
bonding the fiber web to form the water dispersible nonwoven substrate.

22. The method of claim 21, further comprising adding thermoplastic fibers to the individualized fibers and thermal bonding the nonwoven substrate.

23. The method of claim 21, wherein bonding is hydroentangling.

24. The method of claim 21, wherein bonding is mechanical needle punching.

25. The method of claim 21, wherein bonding is passing a heated air stream through the web.

26. The method of claim 21, wherein forming the fiber web is a wet laying process.

27. The method of claim 21, wherein forming the fiber web is dry laying process.

28. A water dispersible nonwoven substrate comprising a majority of individualized bast fibers which are substantially straight, non-cotton, plant-based, and substantially pectin-free and have mean length greater than 4 mm.

29. The water dispersible nonwoven substrate of claim 28, wherein the nonwoven substrate is impregnated with a wetting composition comprising least one additive.

30. The water dispersible nonwoven substrate of claim 29, wherein the at least one additive is a skin care additive, an odor control additive, a de-tackifying agent, a microparticulate, a microcapsule, a preservative, an anti-bacterial agent, a wetting agent, a cleaning agent, a microemulsion, an emollient, a surface feel modifier, a fragrance, a fragrance solubilizer, an opacifier, or a pH control agent.

31. The water dispersible nonwoven substrate of claim 28, wherein the non-cotton, plant-based, and substantially pectin-free fibers are fibers extracted from flax, hemp, jute, ramie, nettle, Spanish broom, kenaf plants, or any combination thereof.

32. The water dispersible nonwoven substrate of claim 28, wherein the non-cotton, plant-based, and substantially pectin-free fibers have less than 10% by weight of the pectin content of the naturally occurring fibers from which the substantially pectin-free fibers are derived.

33. The water dispersible nonwoven substrate of claim 28, wherein the non-cotton, plant-based, and substantially pectin-free fibers have less than 15% by weight of the pectin content of the naturally occurring fibers from which the substantially pectin-free fibers are derived.

34. The water dispersible nonwoven substrate of claim 28, wherein the non-cotton, plant-based, and substantially pectin-free fibers have less than 20% by weight of the pectin content of the naturally occurring fibers from which the substantially pectin-free fibers are derived.

35. The water dispersible nonwoven substrate of claim 28, wherein the non-cotton, plant-based, and substantially pectin-free fibers having a mean length of at least 5 mm.

36. The water dispersible nonwoven substrate of claim 28, wherein the non-cotton, plant-based, and substantially pectin-free fibers have a mean length of at least 6 mm.

37. The water dispersible nonwoven substrate of claim 28, wherein the non-cotton, plant-based, and substantially pectin-free fibers having a mean length of at least 7 mm.

38. The water dispersible nonwoven substrate of claim 28, wherein the non-cotton, plant-based, and substantially pectin-free fibers have a mean length of at least 8 mm.

39. The water dispersible nonwoven substrate of claim 28, wherein the non-cotton, plant-based, and substantially pectin-free fibers have a mean length greater than 9 mm.

40. The water dispersible nonwoven substrate of claim 28, further comprising crimped or straight staple fibers.

41. The water dispersible nonwoven substrate of claim 28, further comprising crimped or straight man-made cellulosic fibers.

42. The water dispersible nonwoven substrate of claim 28, further comprising regenerated cellulosic fibers.

43. The water dispersible nonwoven substrate of claim 28, further comprising wood pulp fibers.

44. The water dispersible nonwoven substrate of claim 28, wherein the nonwoven substrate has a basis weight in a range between about 10 gsm to about 500 gsm.

45. The water dispersible nonwoven substrate of claim 28, wherein the nonwoven substrate is a wet wipe, a dry wipe, or an impregnated wipe.

46. The water dispersible nonwoven substrate of claim 28, wherein the water dispersible nonwoven substrate is a tissue, a facial tissue, a bath tissue, a baby wipe, a personal care wipe, a personal protective wipe, a cosmetic wipe, a perinea wipe, a disposable washcloth, a kitchen wipe, an automotive wipe, a bath wipe, a hard surface wipe, a cleaning wipe, a disinfecting wipe, a glass wipe, a mirror wipe, a leather wipe, an electronics wipe, a lens wipe, a polishing wipe, a medical cleaning wipe, or a disinfecting wipe.

47. The water dispersible nonwoven substrate of claim 28, wherein the nonwoven substrate is hydroentangled.

48. A method of making the water dispersible nonwoven substrate of claim 28, the method comprising:
chemically treating naturally occurring fibers to substantially remove pectin and form substantially individualized fibers;
forming a fiber web; and
bonding the fiber web to form the water dispersible nonwoven substrate.

49. The method of claim 48, further comprising adding thermoplastic fibers to the individualized fibers and thermal bonding the nonwoven substrate.

50. The method of claim 48, wherein bonding is hydroentangling.

51. The method of claim 48, wherein bonding is mechanical needle punching.

52. The method of claim 48, wherein bonding is passing a heated air stream through the web.

53. The method of claim 48, wherein forming the fiber web is a wet laying process.

54. The method of claim 48, wherein forming the fiber web is dry laying process.

55. A water dispersible nonwoven substrate comprising individualized bast fibers with less than 20% of the pectin content of the naturally occurring bundled bast fiber from which the individualized bast fibers are derived, the individualized bast fibers being formed into an unbounded web in the dry state, and the bast fibers having a mean length greater than 4 mm.

56. The water dispersible nonwoven substrate of claim 55, wherein the nonwoven substrate is impregnated with a wetting composition comprising least one additive.

57. The water dispersible nonwoven substrate of claim 56, wherein the at least one additive is a skin care additive, an odor control additive, a de-tackifying agent, a microparticulate, a microcapsule, a preservative, an anti-bacterial agent, a wetting agent, a cleaning agent, a microemulsion, an emollient, a surface feel modifier, a fragrance, a fragrance solubilizer, an opacifier, or a pH control agent.

58. The water dispersible nonwoven substrate of claim 55, wherein the individualized bast fibers are fibers extracted from flax, hemp, jute, ramie, nettle, Spanish broom, kenaf plants, or any combination thereof.

59. The water dispersible nonwoven substrate of claim 55, wherein the individualized bast fibers have less than 10% by weight of the pectin content of the naturally occurring fibers from which the substantially pectin-free fibers are derived.

60. The water dispersible nonwoven substrate of claim 55, wherein the individualized bast fibers have less than 15% by weight of the pectin content of the naturally occurring fibers from which the substantially pectin-free fibers are derived.

61. The water dispersible nonwoven substrate of claim 55, wherein the individualized bast fibers have a mean length of at least 5 mm.

62. The water dispersible nonwoven substrate of claim 55, wherein the individualized bast fibers have a mean length of at least 6 mm.

63. The water dispersible nonwoven substrate of claim 55, wherein the individualized bast fibers have a mean length of at least 7 mm.

64. The water dispersible nonwoven substrate of claim 55, wherein the individualized bast fibers have a mean length of at least 8 mm.

65. The water dispersible nonwoven substrate of claim 55, wherein the individualized bast fibers have a mean length greater than 9 mm.

66. The water dispersible nonwoven substrate of claim 55, further comprising crimped or straight staple fibers.

67. The water dispersible nonwoven substrate of claim 55, further comprising crimped or straight man-made cellulosic fibers.

68. The water dispersible nonwoven substrate of claim 55, further comprising regenerated cellulosic fibers.

69. The water dispersible nonwoven substrate of claim 55, further comprising wood pulp fibers.

70. The water dispersible nonwoven substrate of claim 55, wherein the nonwoven substrate has a basis weight in a range between about 10 gsm to about 500 gsm.

71. The water dispersible nonwoven substrate of claim 55, wherein the nonwoven substrate is a wet wipe, a dry wipe, or an impregnated wipe.

72. The water dispersible nonwoven substrate of claim 55, wherein the water dispersible nonwoven substrate is a tissue, a facial tissue, a bath tissue, a baby wipe, a personal care wipe, a personal protective wipe, a cosmetic wipe, a perinea wipe, a disposable washcloth, a kitchen wipe, an automotive wipe, a bath wipe, a hard surface wipe, a cleaning wipe, a disinfecting wipe, a glass wipe, a mirror wipe, a leather wipe, an electronics wipe, a lens wipe, a polishing wipe, a medical cleaning wipe, or a disinfecting wipe.

73. The water dispersible nonwoven substrate of claim 55, wherein the nonwoven substrate is hydroentangled.

74. A method of making the water dispersible nonwoven substrate of claim 55, the method comprising:
   chemically treating naturally occurring fibers to substantially remove pectin and form substantially individualized fibers;
   forming a fiber web; and
   bonding the fiber web to form the water dispersible nonwoven substrate.

75. The method of claim 74, further comprising adding thermoplastic fibers to the individualized fibers and thermal bonding the nonwoven substrate.

76. The method of claim 74, wherein bonding is hydroentangling.

77. The method of claim 74, wherein bonding is mechanical needle punching.

78. The method of claim 74, wherein bonding is passing a heated air stream through the web.

79. The method of claim 74, wherein forming the fiber web is a wet laying process.

80. The method of claim 74, wherein forming the fiber web is a dry laying process.

\* \* \* \* \*